United States Patent [19]

Naito et al.

[11] 4,446,134

[45] May 1, 1984

[54] PROCESS FOR HEAT TREATMENT OF AQUEOUS SOLUTION CONTAINING HUMAN BLOOD COAGULATION FACTOR VIII

[75] Inventors: Ryoichi Naito, Ibaraki; Tadakazu Suyama, Kyoto; Yoshiro Iga, Nishinomiya, all of Japan

[73] Assignee: The Green Cross Corporation, Osaka, Japan

[21] Appl. No.: 350,150

[22] Filed: Feb. 19, 1982

[30] Foreign Application Priority Data

Oct. 28, 1981 [JP] Japan ................................ 56-173585

[51] Int. Cl.$^3$ ........................................ A61K 35/14
[52] U.S. Cl. .................................. 424/101; 260/112 B
[58] Field of Search ............................... 424/101, 177; 260/112 B

[56] References Cited

U.S. PATENT DOCUMENTS 2,705,230  3/1955  Reid ................................ 260/112 B
4,085,095  4/1978  Bick ................................ 424/101 X
4,297,344  10/1981 Schwinn ........................... 424/101
4,327,086  4/1982  Fukushima ....................... 424/101 X

OTHER PUBLICATIONS

Barrow, Chem. Abs., vol. 81, 1974, Ab No. 134384j.
Barrow, Chem. Abs., vol. 76, 1972, Ab No. 150146k.
Hynes, Chem. Abs., vol. 72, 1970, Ab No. 52736a.
Vlckova, Chem. Abs., vol. 74, 1971, Ab No. 10185j.

Primary Examiner—Sam Rosen
Attorney, Agent, or Firm—Cushman, Darby & Cushman

[57] ABSTRACT

Human blood coagulation factor VIII which may have hepatitis virus activity can be virus-inactivated with keeping at a minimum the damage of the factor VIII by heating its aqueous solution at 50° to 80° C. for 3 to 15 hours in the presence of 10% (W/V) or more of at least one principal stabilizer of neutral amino acids, monosaccharides, oligosaccharides, and sugar alcohols and 10% (W/V) or more of at least one auxiliary stabilizer of salts of hydrocarbon and hydroxyhydrocarbon carboxylic acids having 3 to 10 carbon atoms.

12 Claims, No Drawings

PROCESS FOR HEAT TREATMENT OF AQUEOUS SOLUTION CONTAINING HUMAN BLOOD COAGULATION FACTOR VIII

This invention relates to a process for heat treatment to inactivate the hepatities virus in an aqueous solution containing human blood coagulation factor VIII.

The human blood coagulation factor VIII (hereinafter referred to simply as factor VIII), also called antihemophilic factor A, is one of the blood coagulation factors contained in plasma. A disease caused by the congential deficiency of this factor is what is called hemophilia A. Patients suffering from this disease cannot complete the blood coagulation reaction necessary when hemorrhage occurs, so that even a small injury brings about a large loss of blood.

Factor VIII preparations are widely in use for the purpose of supplying the factor VIII to such patients suffering from the disease due to the congential deficiency or diminution of facter VIII, and for treating or preventing such hemorrhage. In recent years, however, the occurrence of serum hepatitis accompanying blood transfusion or blood constituent transfusion has become a serious social problem and was ascertaind to be caused by the hepatitis virus. Each of human serum protein preparations obtained by fractionating human plasma also involves this problem.

It is also aphrehended that factor VIII compositions to be treated according to this invention, which are one of human serum protein preparations, are contaminated with said hepatitis virus.

In order to solve the problem of hepatitis infection, it was found out that the infectivity of hepatitis virus in human serum protein preparations, particularly in albumin preparations, can be supressed by a heat treatment at 60° C. for 10 hours without denaturating the albumin. However, the substances that said heat treatment can be applied to must be stable under these conditions.

On the contrary, the factor VIII, the subject of this invention, is so instable to heat that its activity becomes markedly deteriorated when an aqueous solution thereof is heated at 60° C. for 10 hours.

The object of this invention is to provide a process for heat treatment to inactivate the virus of hepatitis in an aqueous solution containing human blood coagulation factor VIII.

The present inventors found out that the stability of factor VIII in an aqueous solution against the heat treatment at 60° C. for 10 hours is markedly improved by adding a neutral amino acid, a monosaccharide, an oligosaccharide, or a sugar alcohol to a concentration of 10% or more, and also that the heat stability is more enhanced by further addition of a specific carboxylic acid salt. The present invention has been accomplished on the basis of said finding.

This invention provides a process for heat treatment to inactivate the hepatitis virus in a human blood coagulation factor VIII composition, which comprises carrying out the heat treatment at 50° to 80° C. of an aqueous solution containing the human blood coagulation factor VIII for a time sufficient to inactivate the hepatitis virus but to ratain the activity of the blood coagulation factor VIII in the presence of 10% (W/V) or more of at least one principal stabilizer selected from the group consisting of neutral amino acids, monosaccharides, oligosaccharides and sugar alcohols, and 10% (W/V) or more of at least one auxiliary stabilizer selected from the gruop consisting of salts of hydrocarbon and hydroxyhydrocarbon carboxylic acids, which have 3 to 10 carbon atoms.

The symbol, "% (W/V)", means herein a percentage of a solute by weight per a solution by volume.

The factor VIII, which is the subject of the heat treatment in this invention, is not specifically restricted so far as it is originated from human. Methods of separating and purifying the factor VIII from blood plasma in which it is principally contained, are already known [Johnson A. J. et al., British Journal of Haematology, 21, 21 (1971) and Wagner R. B. et al., Thrombsis Diathesis Haemorrhagica, 11, 64 (1964)].

The factor VIII content in the aqueous solution to be heat-treated is optional but preferably 1 to 50 units/ml in terms of its potency. The pH of the aqueous solution is generally 5 to 10, preferably 6.0 to 8.0, and favorably adjusted thereto with a suitable buffer solution of low salt concentration.

Herein, one unit of factor VIII is defined as a potency equivalent to the activity of factor VIII contained in one milliliter of fresh human plasma, and the potency assay is carried out in accordance with the thromboplastin formation test reported by Pool and Robbinson [British Journal of Haematology, 5, 17 (1959)].

The principal stabilizers to be selected from neutral amino acids, monosaccharides, oligosaccharides, and sugar alcohols include, for example, glycine and alanine as neutral amino acids; glucose, xylose, and fructose as monosaccharides; maltose, sucrose, and lactose as oligosaccharides; and mannitol, galactitol, glucosaminitol, sorbitol, and galactosaminitol as sugar alcohols. These principal stabilizers may be used each alone or in combination. The amount thereof to be added is at least 10% (W/V), preferably 10 to 60% (W/V) in practice.

The hydrocarbon or hydroxyhydrocarbon carboxylic acid of 3 to 10 carbon atoms used for the auxiliary stabilizer is a carboxylated hydrocarbon or carboxylated hydroxyhydrocarbon, and its hydrocarbon or hydroxyhydrocarbon radical may be either saturated or unsaturated. Examples of such hydrocarbon radicals include alkyl, aryl (e.g. phenyl) and aralkyl which may have hydroxyl group. The number of carboxyl groups may be singular or plural, preferably one or two. Although the salt of said carboxylic acid is not particularly restricted so far as it is physiologically acceptable, alkali metal salts (e.g. sodium salt and potassium salt) and alkaline earth metal salts (e.g. calcium salt) are preferred, and sodium salt and potassium salt are especially preferably.

Preferred examples of said carboxylic or hydroxycarboxylic acis salts, which are physiologically acceptable, are alkali metal salts (e.g. sodium salts and potassium salts), of propanoic acid, butanoic acid, pentanoic acid, caproic acid, caprylic acid, malonic acid, succinic acid, glutaric acid, adipic acid, citric acid, and mandelic acid. The amount of carboxylic acid added is at least 10% (W/V) and is 10 to 30% (W/V) in practical.

The addition of a small amount of human albumin besides said stabilizers further improves the heat stability of the factor VIII.

The temperature of heat treatment is 50° to 80° C., preferably about 60° C., and the heating time is restricted to inactivate the hepatitis virus but to retain the practical potency of the blood coagulation factor VIII and is 3 to 15 hours depending on the heating temperature used, preferably about 10 hours at 60° C.

The aqueous solution of factor VIII thus heat-treated shows a strong electric conductivity which is two to five times higher than that of the untreated solution due to the presence of the stabilizers used. For reducing the electric conductivity of the factor VIII solution, treatments of dialysis and dilution with water are done, followed by a precipitating treatment of the factor VIII by adding a precipitant such as glycine or polyethylene glycol to the solution. Alternatively, the solution is diluted with water to reduce the electric conductivity to facilitate the succesive purification of the factor VIII. Thereafter the purification may be performed in known ways. The recovered factor VIII, if already highly purified, is made into medical preparations as it is, by customary pharmaceutical procedures such as sterile filtration, dispensation and lyophilization. When the recovered factor VIII is a crude one, it is highly purified by combining known procedures for the purification of the factor VIII, such as fractionation by use of polyethylene glycol and salting-out treatment.

In order to examine the effectiveness of the heat treatment of this invention, a preparation of the human factor VIII which has been recovered from a $HB_sA_g$ (hepatitis virus antigen)-positive blood plasma was heat-treated at 60° C. for 10 hours in the presence of the above specified stabilizers. A portion of the preparation corresponding to a factor VIII activity of 100 units was inoculated into a chimpanzee and the onset of hepatitis was examined, with the result that no sign of hepatitis was observed even one month after.

As described above, the infectivity of a possible contaminant hepatitis virus in factor VIII compositions, a precious blood product, can be extinguished with keeping at a minimum the damage of factor VIII by the heat treatment process of this invention, which is therefore very effective in the commercial production of factor VIII preparations requiring a virus inactivation step.

This invention will be illustrated in more detail with reference to the following examples, but it is not limited thereto.

EXAMPLE 1

A solution of 3000 units of factor VIII in 100 ml of a 0.02 M tris-0.01 M sodium citrate buffer solution of pH 7.0, after addition of 15 g of glycine and 20 g of sodium caprylate, was heated at 60° C. for 10 hours. The solution was then cooled and the resulting precipitate was removed by centrifugation. The supernatant obtained was dialyzed against a 0.02 M tris-0.01 M sodium citrate buffer solution, sterile-filtered, dispensed, and lyophilized.

EXAMPLE 2

A 30 units/ml solution of factor VIII in 100 ml of a 0.02 M tris-0.01 M sodium citrate buffer solution (pH 7.0), after addition of 15 g of glycine and 20 g of sodium caprylate, was heated at 60° C. for 10 hours. Thereafter, the solution was processed in the same manner as Example 1 to obtain a factor VIII preparation.

EXAMPLE 3

A 100 ml solution of 3000 units of factor VIII in a 0.02 M tris-0.01 M sodium citrate buffer solution of pH 7.0, after addition of 15 g of sodium caprylate, 2 g of human albumin, and 60 g of sucrose, was heated at 60° C. for 10 hours. Thereafter, the solution was processed in the same manner as Example 1 to obtain a factor VIII preparation.

EXPERIMENTAL EXAMPLE

A series of experiments were made to evaluate the stabilizing effect of different stabilizers. In these experiments, one liter of an aqueous solution containing 25-30 units of factor VIII/ml, after addition of each stabilizer in an amount as shown in Table 1, was heated at 60° C. for 10 hours. The percentage of activity retention based on the untreated solution in each case was shown in Table 1. These results have verified that the principal stabilizers, coupled with the auxiliary stabilizers and human albumin, markedly improve the heat stability of factor VIII.

TABLE 1

| Principal stabilizer | W/V % | Auxiliary stabilizer | W/V % | Retention of activity (%) |
|---|---|---|---|---|
| Glycine | 15 | Trisodium citrate | 0 | 30 |
|  |  |  | 10 | 40 |
|  |  |  | 15 | 60 |
|  |  |  | 20 | 60 |
|  |  |  | 20* | 70 |
|  | 25 | Sodium caprylate | 0 | 20 |
|  |  |  | 10 | 45 |
|  |  |  | 15 | 65 |
|  |  |  | 20 | 65 |
|  |  |  | 20* | 70 |
| Alanine | 25 | Sodium citrate | 0 | 10 |
|  |  |  | 10 | 45 |
|  |  |  | 20 | 48 |
|  |  |  | 20* | 65 |
| Mannitol | 15 | Sodium mandelate | 0 | 20 |
|  |  |  | 10 | 40 |
|  |  |  | 15 | 45 |
|  |  |  | 20 | 45 |
|  |  |  | 20* | 45 |
|  | 25 | Sodium caproate | 0 | 25 |
|  |  |  | 10 | 35 |
|  |  |  | 15 | 50 |
|  |  |  | 20 | 60 |
|  |  |  | 20* | 65 |
|  | 15 | Sodium caprylate | 0 | 30 |
|  |  |  | 10 | 45 |
|  |  |  | 15 | 54 |
|  |  |  | 20 | 65 |
|  |  |  | 20* | 70 |
|  | 25 | Sodium caprylate | 0 | 30 |
|  |  |  | 10 | 45 |
|  |  |  | 15 | 55 |
|  |  |  | 20 | 65 |
|  |  |  | 20* | 65 |
| Glucose | 15 | Disodium glutarate | 0 | 15 |
|  |  |  | 10 | 30 |
|  |  |  | 15 | 40 |
|  |  |  | 20 | 40 |
|  |  |  | 20* | 55 |
|  | 25 | Disodium malonate | 0 | 15 |
|  |  |  | 10 | 30 |
|  |  |  | 15 | 40 |
|  |  |  | 20 | 40 |
|  |  |  | 20* | 40 |
| None |  | None |  | 0 |

Note
*Two % (W/V) of human albumin was added.

What is claimed is:

1. A process for heat treatment to inactivate the hepatitis virus in a human blood coagulation factor VIII composition, which comprises carrying out the heat treatment at 50° to 80° C. of an aqueous solution containing the human blood coagulation factor VIII for a time sufficient to inactivate the hepatitis virus but to retain the activity of the blood coagulation factor VIII, said heat treatment conducted in the presence of 10% (W/V) or more of at least one principal stabilizer selected from the group consisting of neutral amino acids, monosaccharides, oligosaccharides, and sugar alcohols and 10% (W/V) or more of at least one auxiliary stabilizer selected from the group consisting of salts of hydrocarbon carboxylic acids and hydroxhydrocarbon carboxylic acids, which have 3 to 10 carbon atoms.

2. A process according to claim 1, wherein the heat treatment is carried out in the additional presence of 0.1% (W/V) or more of human albumin.

3. A process according to claim 1 or 2, wherein the salts of organic carboxylic acids are physiologically acceptable salts of propanoic acid, butanoic acid, pentanoic acid, caprylic acid, caproic acid, malonic acid, succinic acid, glutaric acid, adipic acids, citric acid and mandelic acid.

4. A process according to claim 3, wherein the physiologically acceptable salt is a sodium or a potassium salt.

5. A process according to claim 1 or 2, wherein the neutral amino acid is present and is gylcine or alanine.

6. A process according to claim 1 or 2, wherein the monosaccharide is present and is glucose, xylose or fructose.

7. A process according to claim 1 or 2, wherein the oligosaccharide is present and is maltose, sucrose or lactose.

8. A process according to claim 1 or 2, wherein the sugar alcohol is present and is mannitol, galacititol, glucosaminitol, sorbitol or galactosaminitol.

9. A process according to claim 1 or 2, wherein the principal stabilizer and the auxiliary stabilizer are present in amounts of 10 to 30% (W/V) and 10 to 30% (W/V), respectively.

10. A process according to claim 1 or 2, wherein the auxiliary stabilizer is a salt of hydrocarbon carboxylic acid having 3 to 10 carbon atoms.

11. A process according to claim 1 or 2, wherein the auxiliary stabilizer is a salt of hydroxyhydrocarbon carboxylic acid having 3 to 10 carbon atoms.

12. A process according to claim 1 or 2, wherein the heating time is between 3 and 15 hours (inclusive).

* * * * *